(12) United States Patent
Govari et al.

(10) Patent No.: US 11,896,297 B2
(45) Date of Patent: Feb. 13, 2024

(54) DETECTING AND VISUALIZING BUBBLES FORMED IN MEDICAL PROCEDURE USING SCHLIEREN IMAGES

(71) Applicant: Biosense Webster (Israel) Ltd., Yokneam (IL)

(72) Inventors: Assaf Govari, Haifa (IL); Eran Aharon, Haifa (IL); Amit Fuchs, Hogla (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 156 days.

(21) Appl. No.: 17/239,371

(22) Filed: Apr. 23, 2021

(65) Prior Publication Data
US 2022/0338921 A1   Oct. 27, 2022

(51) Int. Cl.
*A61B 18/14* (2006.01)
*A61B 90/00* (2016.01)
*A61B 18/12* (2006.01)
*A61B 18/00* (2006.01)

(52) U.S. Cl.
CPC ...... *A61B 18/1492* (2013.01); *A61B 18/1206* (2013.01); *A61B 90/36* (2016.02); *A61B 2018/00577* (2013.01)

(58) Field of Classification Search
CPC . A61B 18/1492; A61B 90/36; A61B 18/1206; A61B 2018/00577; A61B 18/14; A61B 90/00; A61B 18/12
See application file for complete search history.

(56) References Cited

U.S. PATENT DOCUMENTS

| | | |
|---|---|---|
| 2004/0049216 A1 | 3/2004 | Verdaasdonk |
| 2005/0203399 A1 | 9/2005 | Vaezy et al. |
| 2008/0319356 A1 | 12/2008 | Cain et al. |
| 2012/0253201 A1* | 10/2012 | Reinhold ............ H04N 13/254 345/419 |
| 2019/0001159 A1 | 1/2019 | Chen et al. |
| 2022/0192598 A1 | 6/2022 | Govari et al. |

(Continued)

FOREIGN PATENT DOCUMENTS

WO   WO 2014/118729 A1   8/2014

OTHER PUBLICATIONS

Marijn Groen, "Feasibility of irreversible electroporation for pulmonary vein isolation", Apr. 2018 (Year: 2018).*

(Continued)

*Primary Examiner* — Linda C Dvorak
*Assistant Examiner* — Abigail Bock
(74) *Attorney, Agent, or Firm* — Troutman Pepper Hamilton Sanders LLP

(57) ABSTRACT

A system for visualizing one or more bubbles formed by a catheter, the system includes a fluid container, a pulse generator, a schlieren imaging assembly, and a processor. The fluid container is configured to: (i) contain a fluid, and (ii) receive into the fluid the catheter having one or more electrodes. The pulse generator is configured to apply one or more pulses to at least one of the electrodes. The schlieren imaging assembly is configured to acquire schlieren images of the bubbles occurring in the fluid when applying the one or more pulses, and the processor is configured to visualize the bubbles using the schlieren images.

18 Claims, 2 Drawing Sheets

(56) References Cited

U.S. PATENT DOCUMENTS

2022/0202480 A1 6/2022 Govari et al.

OTHER PUBLICATIONS

Jan L. Chaloupka & Maurice Woods & Jacob Aas & Jessamyn Hutchins & Jonathan D. Thistle, "Color schlieren imaging with a two-path, double knife edge system", Optics Express, vol. 22, Issue 7, pp. 8041-8046 (Year: 2014).*

"Schlieren imaging: a powerful tool for atmospheric plasma diagnostic"; Traldi, et al. EPJ Techniques and Instrumentation (2018) 5:4; https://doi.org/10.1140/epjti/s40485-018-0045-1; pp. 1-23.

Extended European Search Report dated Sep. 19, 2022, from corresponding EP Application No. 22169355.9.

Verdaasdonk Rudolf: "Schlieren Imaging: Optical Techniques to Visualize Thermal Interactions with Biological Tissues" In: "Handbook of Physics in medicine and Biology", Jan. 1, 2010 (Jan. 1, 2010), CRC Press Taylor & Francis Group, XP055959206, pp. 1-521.

Verdaasdonk Rudolf M. et al: "Imaging techniques for research and education of thermal and mechanical interactions of lasers with biological and model tissues", Journal of Biomedical Optics, vol. 11, No. 4, Jun. 1, 2006 (Jun. 1, 2006), p. 041110, XP055958969, 1000 20th St. Bellingham WA 98225-6705 USA ISSN: 1083-3668, DOI: 10.1117/1.2338817.

Gary S Settles et al: "A review of recent developments in schlieren and shadowgraph techniques", Measurement Science and Technology, IOP, Bristol, GB, vol. 28, No. 4, Feb. 15, 2017 (Feb. 15, 2017), p. 42001, XP020314806, ISSN: 0957-0233, DOI: 10. 1088/1361-6501/AA5748.

P. Kotini: "Detection of microbubble formation during radiofrequency ablation using phonocardiography", EUROPACE, vol. 8, No. 5, Mar. 16, 2006 (Mar. 16, 2006), pp. 333-335, XP055152448, ISSN: 1099-5129, DOI: 10.1093/europace/eu1018.

* cited by examiner

DETECTING AND VISUALIZING BUBBLES FORMED IN MEDICAL PROCEDURE USING SCHLIEREN IMAGES

FIELD OF THE INVENTION

The present invention relates generally to visualization and detection systems, and particularly to methods and systems for detecting bubbles formed in a medical procedure.

BACKGROUND OF THE INVENTION

Schlieren techniques are used for imaging in various applications, such as in some medical imaging.

For example, U.S. Patent Application Publication 2005/0203399 describes a frame ensures that the alignment between a high intensity focused ultrasound (HIFU) transducer designed for vaginal use and a commercially available ultrasound image probe is maintained, so that the HIFU focus remains in the image plane during HIFU therapy. A water-filled membrane placed between the HIFU transducer and the treatment site provides acoustic coupling. The coupling is evaluated to determine whether any air bubbles exist at the coupling interface, which might degrade the therapy provided by the HIFU transducer.

U.S. Patent Application Publication 2004/0049216 describes a device for perforating tissue, especially for transmyocardial revascularisation, the device comprising an ultrasonic generator coupled to an attachable solid needle.

As shown in FIGS. 1a-1i of the publication "SCHLIEREN IMAGING: A POWERFUL TOOL FOR ATMOSPHERIC PLASMA DIAGNOSTIC" by Enrico Traldil, Marco Bosellil, Emanuele Simoncellil, Augusto Stancampiano, Matteo Gherardil, Vittorio Colombo and Gary S. Settles, published by EPJ Techniques and Instrumentation (2018), which is incorporated by reference herein, eight different arrangements (shown in this publication as FIGS. 1b, 1c, 1d, 1e, 1f, 1g, 1h and 1i) of the Schlieren imaging technique can be utilized from the Schlieren technique first invented by August Toepler in 1859 (shown in FIG. 1a of this publication).

SUMMARY OF THE INVENTION

An embodiment of the present invention that is described herein provides a system for visualizing one or more bubbles formed by a catheter, the system includes a fluid container, a pulse generator, a schlieren imaging assembly, and a processor. The fluid container is configured to: (i) contain a fluid, and (ii) receive into the fluid the catheter having one or more electrodes. The pulse generator is configured to apply one or more pulses to at least one of the electrodes. The schlieren imaging assembly is configured to acquire schlieren images of the bubbles occurring in the fluid when applying the one or more pulses, and the processor is configured to visualize the bubbles using the schlieren images.

In some embodiments, the fluid is at least partially transparent, and the schlieren imaging assembly is configured to acquire two-dimensional (2D) schlieren images of the fluid. In other embodiments, the schlieren imaging assembly includes: (i) a first lens, positioned at a first side of the fluid container, and configured to direct a collimated light beam through the fluid, and (ii) a second lens, positioned at a second side of the fluid container, opposite the first side, and configured to produce, based on the collimated light beam, a focused light beam for visualizing the bubbles.

In an embodiment, the schlieren imaging assembly includes: (i) a knife-edge, which is configured to partially block the focused light beam, and (ii) a camera, which is configured to produce, based on the partially-blocked focused light beam, an image indicative of the bubbles. In another embodiment, at least one of the pulses applied by the pulse generator includes an ablation pulse, and at least one of the electrodes includes an ablation electrode, which is configured to apply at least the ablation pulse to tissue of a patient organ.

There is additionally provided, in accordance with an embodiment of the present invention, a method for visualizing one or more bubbles formed by a catheter, the method includes receiving, into a fluid contained in a fluid container, the catheter having one or more electrodes. One or more pulses are applied to at least one of the electrodes. Schlieren images of the bubbles occurring in the fluid when applying the one or more pulses, are acquired, and the bubbles are visualized using the schlieren images.

The present invention will be more fully understood from the following detailed description of the embodiments thereof, taken together with the drawings in which:

DETAILED DESCRIPTION OF EMBODIMENTS

Overview

Figure 1:
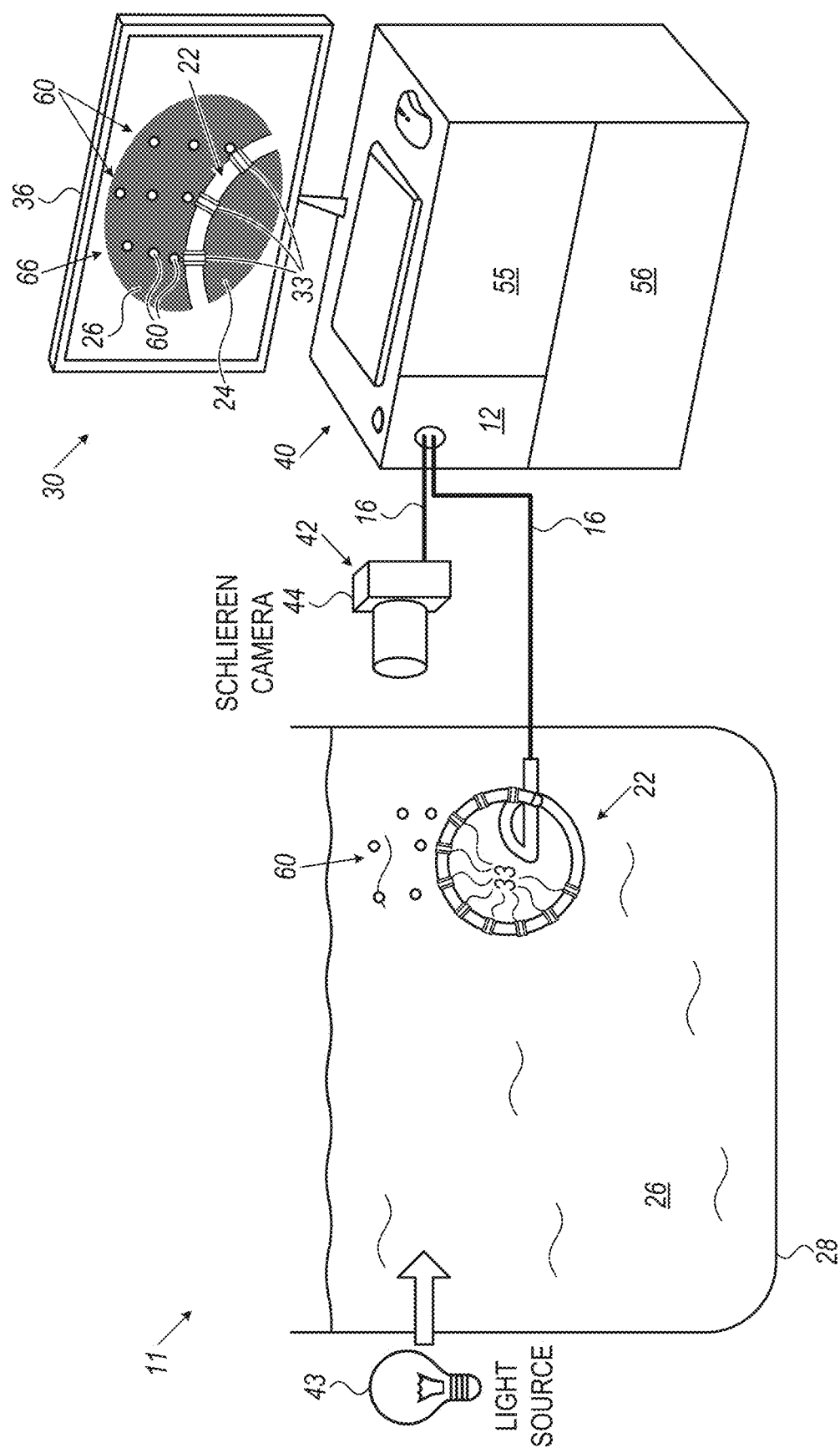
FIG. 1 is a schematic, pictorial illustration of a system for detecting and visualizing bubbles that may occur in an ablation procedure, in accordance with an embodiment of the present invention.

In a catheterization procedure, such as in radiofrequency (RF) ablation and irreversible electroporation (IRE) carried out in a patient heart, it is important to prevent formation of bubbles that may occur, e.g., in the blood, when ablating tissue of the heart. For example, micro bubbles having a sub-millimeter diameter, which may undesirably occur during a cardiac ablation procedure, may be transferred with the blood stream to the brain, and may cause, for example, an ischemic stroke in the brain. Thus, it is important to test ablation catheters, so as to prevent or minimize the formation of such bubbles or micro bubbles in the blood during the catheterization procedure.

Embodiments of the present invention that are described hereinbelow provide methods and systems for testing a catheter, so as to detect and visualize one or more bubbles or micro bubbles that may occur during catheterization, such as an RF ablation procedure.

In some embodiments, a system for detecting and/or visualizing one or more bubbles formed by a catheter, comprises: (a) a fluid container, (b) a pulse generator, (c) a schlieren imaging assembly, and (d) a processor. Note that the system is typically positioned in a laboratory or in a quality assurance section of a catheter production facility.

The system is configured to serve for improving and/or testing the RF ablation catheter (also referred to herein as a catheter, for brevity) by detecting and/or visualizing bubbles that may occur when applying ablation pulses to ablation electrodes of the catheter, as described in detail below.

In some embodiments, the fluid container is transparent to light and is configured to contain a fluid, which is typically transparent. The fluid container is further configured to receive into the fluid a catheter having one or more ablation electrodes, which are configured for applying ablation pulses to the fluid within the container. In the present configuration, the bubbles are formed within the fluid (e.g., water, or any other fluid that resembles the blood) placed within the fluid container and surrounding the catheter. Subsequently, the bubbles move toward the surface of the water.

In some embodiments, the pulse generator is configured to apply the RF ablation pulses to one or more ablation electrodes of the ablation catheter. In such embodiments, in case bubbles are formed in the water in response to the applied ablation pulses, the system is configured to detect and/or visualize the bubbles formation.

In some embodiments, the schlieren imaging assembly comprises an illumination source, configured to emit any suitable light beam (e.g., visible light), and a schlieren camera. The schlieren camera is configured to acquire schlieren images of the water, so as to detect bubbles occurring in the water when applying the ablation pulses, through the ablation electrodes, to the water.

In some embodiments, the schlieren imaging assembly comprises: (i) a first lens, which is positioned at a first side of the fluid container, and is configured to direct a collimated light beam through the water, and (ii) a second lens, which is positioned at a second side of the water container, opposite the first side, and is configured to produce, based on the collimated light beam passed through the water, a focused light beam for visualizing the bubbles.

In some embodiments, the schlieren imaging assembly comprises: (i) a knife-edge, which is configured to partially block the focused light beam, and (ii) a camera, which is configured to produce, based on the partially-blocked focused light beam, an image indicative of the bubbles. Note that in the presence of bubbles, at least a portion of the collimated light beam is deflected, and therefore, is not reaching the camera. In such embodiments, the image produced by the camera may comprise a contour or any other indication of a shadow figure caused by the bubbles.

In some embodiments, the processor is configured to visualize and display the bubbles using the schlieren images. In the present example, the camera is configured to produce two-dimensional (2D) schlieren images.

In other embodiments, the system may comprise multiple schlieren imaging assemblies positioned at different orientations relative to the catheter for producing multiple 2D images, and the processor is configured to produce, based on the multiple 2D images, a three-dimensional (3D) schlieren image.

The disclosed techniques improve the quality of catheters, and in particular the quality of RF ablation catheters and the electrodes thereof. Moreover, the disclosed techniques improve the patient safety in catheterization procedures, such as in RF ablation, by testing and preventing the formation of bubbles, before the catheters are being used during RF ablation or during any other catheterization procedure.

System Description

FIG. 1 is a schematic, pictorial illustration of a system 11 for detecting and visualizing bubbles that may occur during an ablation procedure, in accordance with an embodiment of the present invention.

In some embodiments, system 11 may be used for characterizing catheters during product development, and/or for testing catheters during production.

In some embodiments, system 11 comprises a fluid container 28, a schlieren imaging assembly 42, a pulse generator 12, and a control console 30. In the present example, pulse generator 12 is assembled within console 30, and is configured to apply radiofrequency (RF) ablation pulses (or irreversible electroporation (IRE) pulses) to ablation electrodes 33 described in detail below. In other embodiments, pulse generator 12 may be assembled in system 11 using any other suitable configuration (e.g., external to console 30).

In some embodiments, schlieren imaging assembly 42 comprises a schlieren camera 44 described below, and an illumination source 43, which is configured to direct light beams having any suitable wavelength or range of wavelengths. In the present example, illumination source 43 is configured to direct a green light beam having a wavelength of about 550 nm, but in other embodiments, illumination source 43 may direct one or more light beams having any other suitable wavelength or range of wavelengths. For example, a visible light having a wavelength between about 400 nm and 750 nm.

In some embodiments, illumination source 43 may comprise any suitable type of light source, such as but not limited to a white light emitting diode (LED) light source or a light source configured to emit a light beam having any visible light.

In some embodiments, illumination source 43 comprises a coherent light source, which is configured to emit light beams having zero or constant phase difference and same frequency. Moreover, schlieren imaging assembly 42 is configured to emit collimated light beams, which may be produced by illumination source 43, or by optics (not shown) of schlieren imaging assembly 42.

In the context of the present disclosure and in the claims, the terms "about" or "approximately" for any numerical values or ranges indicate a suitable dimensional tolerance that allows the part or collection of components to function for its intended purpose as described herein.

In some embodiments, fluid container 28 is typically made from glass or plastic or any other suitable material, which is transparent at least to the light beam directed by illumination source 43. Fluid container 28 is configured to contain a liquid, which is at least partially transparent to the light beam directed by illumination source 43, and to any other selected wavelength or range of wavelengths. In the present example, the liquid comprises water 26 having minerals and other features for resembling the patient blood. For example, water 26 may comprise one or more minerals selected from a list of eight essential minerals of the human blood (e.g., sodium (Na), calcium (Ca), magnesium (Mg), potassium (K), iron (Fe), zinc (Zn), copper (Cu), and selenium (Se)), and maintained at a temperature between about 36° C. and 38° C. In other embodiments, fluid container 28 may contain water without additives, or may contain any other substance, and/or be maintained at any other suitable temperature.

In some embodiments, fluid container 28 is configured to receive into water 26, one or more catheters 22, in the present example a single lasso-type ablation catheter, but in other embodiments, catheter 22 may comprise any other suitable type of probe, or several catheters tested in fluid container 28 at the same time.

In an embodiment, catheter 22 has one or more ablation electrodes 33, which are configured to apply the aforementioned RF ablation pulses to water 26 contained within container 28.

During an RF ablation procedure, it is important to prevent formation of bubbles that may occur, e.g., in the blood, when ablating tissue of the patient heart. For example, during a cardiac ablation procedure, one or more ablation electrodes 33 may be placed in contact with the patient blood, and bubbles may be formed in the blood when applying the ablation pulses to the tissue. In some cases, the bubbles may comprise micro bubbles having a diameter smaller than about 1 millimeter. Such micro bubbles may be transferred with the blood stream into the brain, and may cause severe damage in the brain, such as an ischemic stroke. Thus, it is important to characterize and test ablation catheters, so as to prevent or minimize the formation of such bubbles or micro bubbles in the patient body during the RF ablation procedure.

In some embodiments, schlieren camera 44 of schlieren imaging assembly 42, is configured to acquire two-dimensional (2D) schlieren images of water 26 when applying the RF ablation pulses to electrodes 33. In the present example, schlieren camera 44 comprises an Alpha A7 III camera, produced by Sony Corporation (Tokyo, Japan), or any other suitable type of camera. Schlieren imaging assembly 42 and the formation of the schlieren images are described in detail in FIG. 2 below.

In some embodiments, schlieren camera 44 is configured to sense an indication of the presence of bubbles or micro bubbles at respective locations within the field of view (FOV) of schlieren camera 44.

In some embodiments, control console 30 comprises a processor 55, typically a general-purpose computer, with suitable front end and interface circuits for receiving signals from schlieren camera 44 and for controlling (by sending control signals, via electrical cables 16 to) several components of system 11, such as but not limited to pulse generator 12, schlieren camera 44 and illumination source 43 of schlieren imaging assembly 42.

In some embodiments, processor 55 may be programmed in software to carry out the functions that are used by the system, and the processor stores data for the software in a memory 56 of console 30. The software may be downloaded to console 30 in electronic form, over a network, for example, or it may be provided on non-transitory tangible media, such as optical, magnetic or electronic memory media. Alternatively, some or all of the functions of processor 55 may be carried out by dedicated or programmable digital hardware components.

In some embodiments, control console 30 comprises a display 36 for displaying information and images described below, and input devices 40.

In some embodiments, processor 55 is configured to receive from schlieren camera 44, via electrical cable 16, signals indicative of the one or more schlieren images acquired when applying the ablation pulses from pulse generator 12, via electrodes 33, to water 26.

In some embodiments, processor 55 is configured to visualize water 26 using the schlieren images received from schlieren camera 44. Based on the schlieren image acquired in a field-of-view (FOV) of schlieren camera 44, processor 55 is configured to display, on display 36 of control console 30, an image 66, which is a visualization of water 26 and an indication of bubbles that may be formed when applying the ablation pulses by electrodes 33, as described above. In the present example, image 66 shows bubbles 60 occurring in water 26 when applying the RF ablation pulses to electrodes 33.

In some embodiments, schlieren imaging assembly 42 may comprise multiple illumination sources (not shown) such as illumination source 43, each of which configured to direct a light beam having one or more predefined wavelengths, and one or more schlieren cameras 44, configured to acquire the schlieren images. For example, schlieren imaging assembly 42 may comprise (i) a first schlieren camera 44, which is configured to acquire a first schlieren image at a first viewing angle relative to the orientation of catheter 22, and (ii) a second schlieren camera (not shown) which is configured to acquire a second schlieren image at a second viewing angle, different from the first viewing angle.

In some embodiments, at least one of, and typically all of, the schlieren images comprise two-dimensional (2D) schlieren images, acquired from different viewing angles. In an embodiment, processor 55 is configured to visualize bubbles that may be undesirably formed between water 26 and electrodes 33 of catheter 22 by producing, based on the 2D schlieren images acquired from two or more different viewing angles, one or more three-dimensional (3D) schlieren images.

In some embodiments, processor 55 is configured to display a time-series of 3D schlieren images shown in video (e.g., a video clip produced using the thirty frames of schlieren images per second, as described above).

This method of using schlieren imaging for testing functionality of catheters is described in detail, for example, in U.S. patent application Ser. No. 17/133,989 and Ser. No. 17/130,459, whose disclosures are all incorporated herein by reference.

This particular configuration of system 11 is shown by way of example, in order to illustrate certain problems that are addressed by embodiments of the present invention and to demonstrate the application of these embodiments in enhancing the performance of such a visualization and/or testing system. Embodiments of the present invention, however, are by no means limited to this specific sort of example system, and the principles described herein may similarly be applied to other sorts of visualizing and/or testing systems.

Apparatus for Detecting and Imaging Bubbles Occurring During RF Ablation

Figure 2:
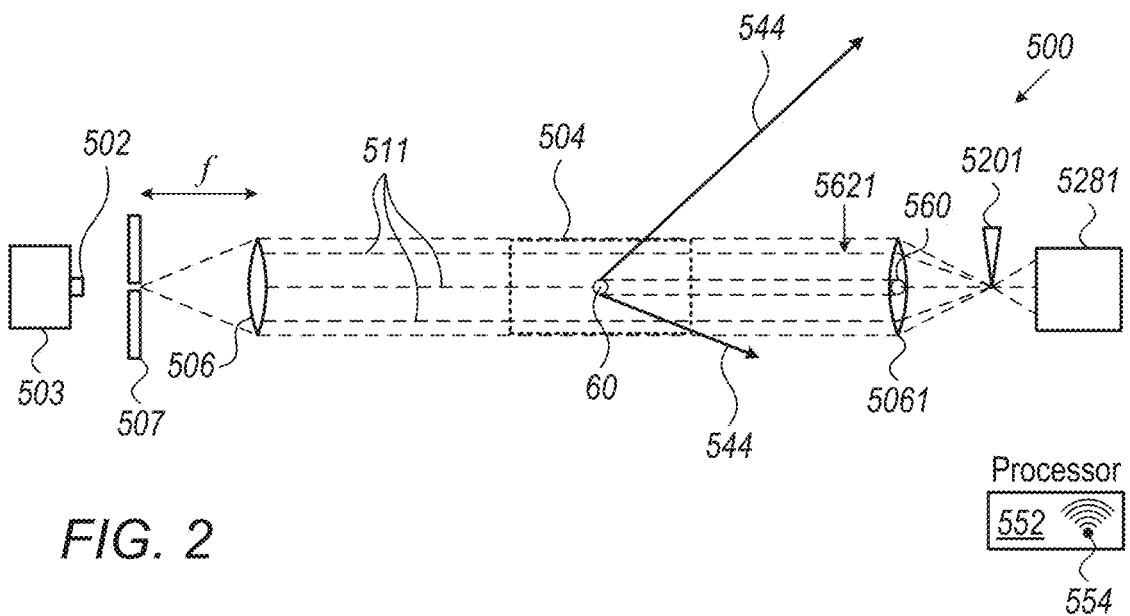
FIG. 2 is a schematic side view of an apparatus used for detecting and visualizing bubbles that may occur in an ablation procedure, in accordance with an embodiment of the present invention.

FIG. 2 is a schematic side view of an apparatus 500 used for detecting and visualizing bubbles that may occur in an ablation procedure, in accordance with an embodiment of the present invention. Apparatus 500 may replace, for example, at least part of schlieren imaging assembly 42 of FIG. 1 above.

In some embodiments, apparatus 500 comprises a bright monochromatic light source, such as a light emitting diode (LED) 502 that is thermally coupled to a heat sink 503. LED 502 may replace, for example, illumination source 43 of FIG. 1 above. In some embodiments, LED 502 together with a pinhole 507 and a lens 506 (comprising a lens assembly of one or more lenses), which is positioned at a focal length f from pinhole 507, form a source of a plane wave of collimated light beam 511, incident through the optical path of apparatus 500.

In some embodiments, the plane wave of collimated light beam 511 is transmitted to incident water 66 contained in fluid container 28 and positioned between lenses 506 and

5061 of apparatus 500. In the present example, a bubble 60 is undesirably formed in water 26, when applying the RF ablation pulses to electrodes 33 of catheter 22, and bubble 60 moves within water 26, so as to reach the surface of water 66 in fluid container 28. Bubble 60 may comprise a micro bubble having a diameter smaller than about 1 mm, as described in FIG. 1 above, or a larger bubble. The plane wave of collimated light beam 511 passes into a field-of-view (FOV) 504 of a video camera 5281 described below, and produces a plane wave 5621, which contains information of water 26.

In some embodiments, apparatus 500 comprises a lens 5061 comprising an assembly of one or more lenses, which is configured to focus the collimated light of plane wave 5621 onto a knife-edge 5201. In some embodiments, knife-edge 5201 is configured to partially block the focused light beam. Note that lens 506 is positioned at a first side of fluid container 28, whereas lens 5061 is positioned at a second side of fluid container 28, opposite the first side. For example, in the configuration of FIG. 1 above, lens 506 is positioned between illumination source 43 and the first side of fluid container 28, and lens 5061 is positioned between the second side of fluid container 28, and schlieren camera 44.

In some embodiments, apparatus 500 further comprises video camera 5281 having suitable optics configured for acquiring the focused beam passing through knife-edge 5201, and producing a 2D schlieren images of the focused light beam captured within FOV 504. Video camera 5281 may replace, for example, camera 44 of FIG. 1 above.

In some embodiments, the components of apparatus 500 are controlled a processor 552, using electrical leads (not shown) and/or one or more wireless communication devices (WCDs) 554, depending on the system design. Processor 552 may replace, for example, processor 55 of FIG. 1 above.

In the present example, light beam 511 is deflected by bubble 60 to produce one or more deflected light beam(s) 544. Since bubble 60 blocks at least part of light beam 511, a shadow FIG. 560 of the bubble is formed on lens 5061, and is imaged in the 2D schlieren image by video camera 5281.

In some embodiments, apparatus 500 is configured to produce a time-series of 2D schlieren images corresponding to respective time instances of bubbles 60 occurring in water 26 when applying one or more RF ablation pulses to one or more electrodes 33.

In other embodiments, apparatus 500 may comprise one or more additional detectors (not shown), which are configured to detect one or more deflected light beam(s) 544, and to produce a signal indicative of deflected light beam(s) 544. In such embodiments, processor 552 is configured to display (i) shadow FIG. 560 on the 2D schlieren image produced by video camera 5281, which is indicative of bubble 60, and (ii) the signal produced in response to detecting deflected light beam(s) 544, which is also indicative of the presence of bubble 60. Note that each of the two indications of bubble 60 have improved contrast relative to 2D images acquired using other imaging techniques, such as any sort of regular optical microscopy based on visible light. It will be understood that detection of bubbles, and particularly of micro bubbles is essential for patient safety in ablation procedures, therefore, improving the contrast can make the difference between designing a safe catheter, as well as releasing or disqualifying a faulty catheter.

In some embodiments, system 11 of FIG. 1 above may comprise multiple schlieren imaging assemblies (such as apparatus 500), positioned at different orientations relative to catheter 22 for producing multiple 2D images. In such embodiments, processor 55 (or processor 552) is configured to produce, based on the multiple 2D images, a three-dimensional (3D) schlieren image.

The configuration of apparatus 500 is simplified for the sake of conceptual clarity and is provided by way of example. In other embodiments, processor 55 of system 11 (shown in FIG. 1 above) may be used in addition to or instead of processor 552, and additional components of the optical path may be added.

Detecting Bubbles Occurring During RF Ablation Using Schlieren Imaging Assembly

Figure 3:
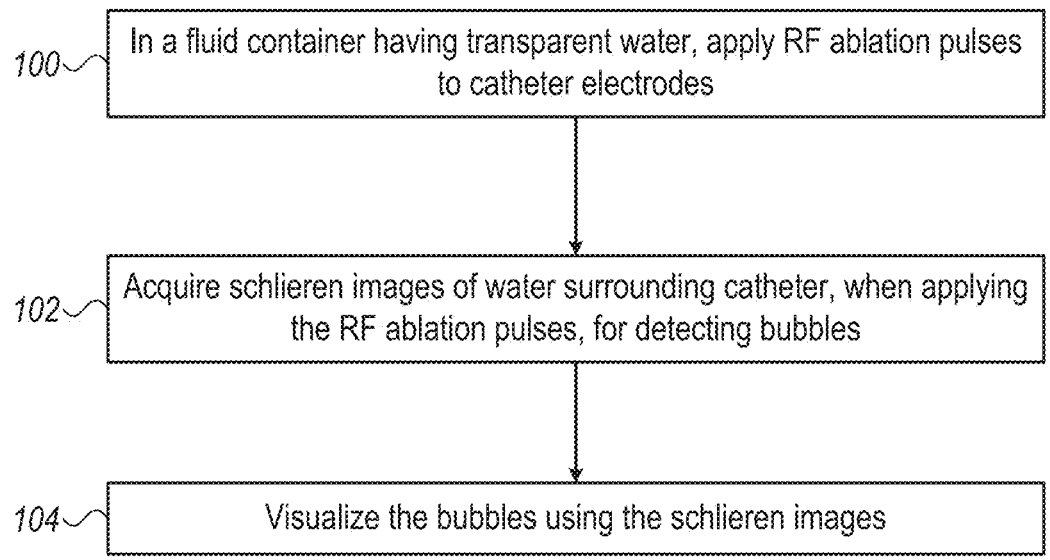
FIG. 3 is a flow chart that schematically illustrates a method for detecting and visualizing bubbles that may occur in an ablation procedure, in accordance with an embodiment of the present invention.

FIG. 3 is a flow chart that schematically illustrates a method for detecting and visualizing bubbles 60 that may occur during a catheterization procedure, such as an RF ablation procedure, in accordance with an embodiment of the present invention.

The method begins at an ablation pulse application step 100, with receiving into water 26 contained in fluid container 28, catheter 22 having one or more ablation electrodes 33, and applying one or more RF ablation pulses (e.g., by pulse generator 12, which is controlled by processor 55 or 552) to at least one of ablation electrodes 33.

At a schlieren images acquisition step 102, when applying the RF ablation pulses, collimated light beam 511 is applied through water 26 positioned between lenses 506 and 5061, which constitutes a section of the optical path of apparatus 500 shown in FIG. 2 above. Note that water 26 is surrounding catheter 22 (as shown in FIG. 1 above) and in case one or more bubbles 60 are formed between electrodes 33 and water 26, apparatus 500 is configured to detect bubble 60 as described in detail in FIG. 2 above.

At a bubble visualization step 104 that concludes the method, processor 55 and/or 552 produces image 66 for visualizing one or more bubbles 60 using the schlieren images acquired by schlieren camera 44 and/or by video camera 5281 of apparatus 500. As described in FIGS. 1 and 2 above, the visualization of one or more bubbles 60 may comprise: (i) one or more 2D schlieren images and/or a video clip for visualizing bubbles 60, and/or (ii) one or more 3D schlieren images produced based on the aforementioned two or more 2D schlieren images acquired from by two or more cameras positioned in two or more different viewing angles, respectively.

Although the embodiments described herein mainly address visualization of bubbles occurring during RF ablation procedures, the methods and systems described herein can also be used in other applications, such as in detection and/or visualization of other undesired elements, such as clusters or blood clots produced in the blood or in any other fluid in a patient organ.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system for visualizing one or more bubbles formed by a catheter, the system comprising:
  a fluid container, configured to: (i) contain a fluid, and (ii) receive into the fluid the catheter having one or more electrodes;
  a pulse generator, configured to apply one or more pulses to at least one of the electrodes;
  a schlieren imaging assembly, configured to acquire schlieren images of the bubbles occurring in the fluid when applying the one or more pulses; and
  a processor, which is configured to visualize the bubbles using the schlieren images.

2. The system according to claim 1, wherein the fluid is at least partially transparent, and wherein the schlieren imaging assembly is configured to acquire two-dimensional (2D) schlieren images of the fluid.

3. The system according to claim 2, wherein the schlieren imaging assembly comprises: (i) a first lens, positioned at a first side of the fluid container, and configured to direct a collimated light beam through the fluid, and (ii) a second lens, positioned at a second side of the fluid container, opposite the first side, and configured to produce, based on the collimated light beam, a focused light beam for visualizing the bubbles.

4. The system according to claim 3, wherein the schlieren imaging assembly comprises: (i) a knife-edge, which is configured to partially block the focused light beam, and (ii) a camera, which is configured to produce, based on the partially-blocked focused light beam, an image indicative of the bubbles.

5. The system according to claim 1, wherein at least one of the pulses applied by the pulse generator comprises an ablation pulse, and wherein at least one of the electrodes comprises an ablation electrode, which is configured to apply at least the ablation pulse to tissue of a patient organ.

6. The system according to claim 1, wherein the schlieren imaging assembly is a first schlieren imaging assembly, the schlieren images are first schlieren images, and the system further comprises:
  a second schlieren imaging assembly, configured to acquire second schlieren images of the bubbles at a second viewing angle different from a first viewing angle of the first schlieren imaging assembly.

7. The system according to claim 1, wherein the processor is configured display a time-series of 3D schlieren images shown in video.

8. The system according to claim 1, wherein the schlieren images of the bubbles comprise 2D schlieren images that are acquired from two or more different viewing angles.

9. The system according to claim 8 wherein the processor is configured to produce one or more three-dimensional (3D) schlieren images based on the 2D schlieren images that are acquired from the two or more different viewing angles.

10. A method for visualizing one or more bubbles formed by a catheter, the method comprising:
  receiving into a fluid contained in a fluid container, the catheter having one or more electrodes;
  applying one or more pulses to at least one of the electrodes;
  acquiring schlieren images of the bubbles occurring in the fluid when applying the one or more pulses; and
  visualizing the bubbles using the schlieren images.

11. The method according to claim 10, wherein applying the one or more pulses comprises applying at least an ablation pulse, and wherein acquiring schlieren images comprises acquiring the schlieren images of the bubbles occurring in the fluid when applying at least the ablation pulse.

12. The method according to claim 10, wherein the schlieren images are first schlieren images acquired at a first viewing angle, and further comprising:
  acquiring second schlieren images of the bubbles at a second viewing angle different from the first viewing angle.

13. The method according to claim 10, further comprising:
  displaying a time-series of 3D schlieren images shown in video.

14. The method according to claim 10, wherein the fluid is at least partially transparent, and wherein acquiring the schlieren images comprises acquiring two-dimensional (2D) schlieren images of the fluid.

15. The method according to claim 14, wherein acquiring the schlieren images comprises: (i) directing, from a first side of the fluid contained, directing a collimated light beam through the fluid, and (ii) producing, based on the collimated light beam at a second side of the fluid container, opposite the first side, a focused light beam for visualizing the bubbles.

16. The method according to claim 15, wherein acquiring the schlieren images comprises: (i) partially blocking the focused light beam, and (ii) producing, based on the partially-blocked focused light beam, an image indicative of the bubbles.

17. The method according to claim 10, wherein the schlieren images of the bubbles comprise 2D schlieren images that are acquired from two or more different viewing angles.

18. The method according to claim 17, further comprising:
  producing one or more 3D schlieren images based on the 2D schlieren images that are acquired from the two or more different viewing angles.

* * * * *